US012702796B2

(12) United States Patent
Collins et al.

(10) Patent No.: US 12,702,796 B2
(45) Date of Patent: Aug. 11, 2026

(54) VIEW-BASED ROBOTIC INTRA-CARDIAC CATHETER GUIDANCE

(71) Applicant: Siemens Medical Solutions USA, Inc., Malvern, PA (US)

(72) Inventors: Jarrod Collins, Wilsonville, OR (US); Young-Ho Kim, West Windsor, NJ (US); Tommaso Mansi, Plainsboro, NJ (US); Sebastien Piat, Lawrence Township, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 192 days.

(21) Appl. No.: 18/474,287

(22) Filed: Sep. 26, 2023

(65) Prior Publication Data

US 2025/0099717 A1 Mar. 27, 2025

(51) Int. Cl.

| | |
|---|---|
| ***A61M 25/01*** | (2006.01) |
| ***A61B 8/12*** | (2006.01) |
| ***A61B 34/10*** | (2016.01) |
| ***A61B 34/30*** | (2016.01) |

(52) U.S. Cl.

CPC ........... *A61M 25/0113* (2013.01); *A61B 8/12* (2013.01); *A61B 34/10* (2016.02); *A61B 34/30* (2016.02); *A61B 2034/107* (2016.02); *A61B 2034/301* (2016.02)

(58) Field of Classification Search

CPC ...... A61M 25/0113; A61B 8/12; A61B 34/10; A61B 34/30; A61B 2034/107

See application file for complete search history.

(56) References Cited

U.S. PATENT DOCUMENTS

| | | | | |
|---|---|---|---|---|
| 2010/0312095 | A1* | 12/2010 | Jenkins .................. | A61B 5/418 600/411 |
| 2021/0145412 | A1* | 5/2021 | Mansi .................... | G06N 3/084 |
| 2022/0202500 | A1* | 6/2022 | Ninni ..................... | A61B 34/25 |
| 2024/0268894 | A1* | 8/2024 | Buil ....................... | A61B 34/20 |

OTHER PUBLICATIONS

Extended European Search Report (EESR) mailed Jan. 27, 2025 in counterpart European patent application No. 24202096.4.

Kim Young-Ho et al: "Automated catheter tip repositioning for intra-cardiac echocardiography"; International Journal of Computer Assisted Radiology and Surgery,; Springer International Publishing, Cham; vol. 17; No. 8; Apr. 25, 2022; pp. 1409-1417.

Kim et.al., "Towards Automatic Manipulation of Intra-cardiac Echocardiography Catheter", arXiv preprint arXiv:2009.05859, 2020, pp. 1-13.

Lee, Dong-Ho, et al. "Non-linear hysteresis compensation of a tendon-sheath-driven robotic manipulator using motor current." IEEE Robotics and Automation Letters 6.2, 2021, pp. 1224-1231.

(Continued)

*Primary Examiner* — Abby Lin
*Assistant Examiner* — Renee LaRose

(57) ABSTRACT

For view-dependent control, different desired imaging catheter views are defined. A robotic catheter system may alter from one view to another view based on activation but otherwise hands-free by the operator. This pre-definition of views and swapping views intra-operatively provides procedure monitoring information while avoiding radiation and minimizing interruption of the procedure (e.g., needle placement and puncture).

16 Claims, 4 Drawing Sheets

(56) References Cited

OTHER PUBLICATIONS

Niederst et al., "Image Processing Pitfalls in Vendor Adaptive Radiotherapy Software with Tomotherapy-like Systems: Feedback from Clinical Case Reports", Current Medical Imaging, 2023, 19, pp. 1156-1166.
Stockigt et al. "Complication prevention in ablation procedures: how to perform transseptal puncture safely in case of atrial septum aneurysm", Heart Rhythm Case Rep, 5(11), pp. 529-533, 2019.
Wikipedia, "Probabilistic Roadmap," downloaded Sep. 19, 2023; 2 pp.
Yang Wang et al. "Learning-based Detection and Tracking in Medical Imaging: A Probabilistic Approach", Lecture Notes in Computational Vision and Biomechanics, vol. 7, 2013; pp. 209-235.
Zhang et al.; "Zero-fluoroscopy transseptal puncture guided by right atrial electroanatomical mapping combined with intracardiac echocardiography: a single-center experience", Clinical Cardiology, 43(9), pp. 1009-1016, 2020.

* cited by examiner

VIEW-BASED ROBOTIC INTRA-CARDIAC CATHETER GUIDANCE

BACKGROUND

The present embodiments relate to robotic control of a medical catheter. One example medical catheter is an intra-cardiac echocardiography (ICE) catheter, which is used for imaging in cardiac interventional and diagnostic procedures. ICE can provide close feedback of anatomical structures and tools during a surgical procedure. Other imaging catheters include optical imaging or guidance catheters.

Due to coronary anatomy, the left atrium is difficult to access for interventional treatment. Transseptal puncture is a technique for creating a small surgical passage through the atrial septum to access the left atrium by catheter from the right atrium. Transseptal catheterization is routinely used for numerous ablation procedures, occlusion of left atrial appendages, and mitral valve repair, among others.

The sole use of biplane fluoroscopy for indirect anatomic landmark guidance has been shown to result in safe and successful transseptal puncture procedures. Radiation exposure from fluoroscopy is of major concern to both doctors and patients. Zero-fluoroscopy transseptal puncture is now possible by replacing fluoroscopic guidance with ICE guidance. Direct visualization of the correct puncture site using ICE can be successfully applied to minimize risk for cardiac injuries. Typical ICE for electrophysiology provides a two-dimensional echocardiogram (i.e., one image sector) and therefore provides limited information about the atrial septum (a 3D surface). Therefore, it is necessary to continuously adjust the position of the ICE catheter during a transseptal puncture procedure to ensure that the incident angle of the transseptal needle is correct. This is inefficient and time-consuming because it requires the physician to remove their hands from the transseptal needle to maneuver the ICE catheter to gain a new imaging perspective. Furthermore, and for the same reason, the ICE catheter cannot be effectively used to track the dynamic movement of the transseptal needle assembly, preventing visualization of the needle tip in critical moments. In its current state, while ICE does provide a clear route towards zero fluoroscopy transseptal puncture, the limitations of ICE regarding control and real-time image adjustment hinder its application for zero-fluoroscopy or reduced fluoroscopy transseptal puncture.

SUMMARY

By way of introduction, the preferred embodiments described below include methods, systems, and robots for view-dependent control. Different desired imaging catheter views are defined. A robotic catheter system may alter from one view to another view based on activation but otherwise hands-free by the operator. This pre-definition of views and swapping views intra-operatively provides procedure monitoring information while avoiding radiation and minimizing interruption of the procedure (e.g., needle placement and puncture).

In a first aspect, a method is provided for robotic control of an imaging catheter. A plurality of views by the imaging catheter in a heart are determined for transseptal puncture. A trajectory of movement of the imaging catheter between the views of the plurality is defined. A robotic catheter system moves the imaging catheter between the views of the plurality along the trajectory. Images from the imaging catheter at the views of the plurality are displayed.

In a second aspect, a catheter control system is provided. A memory is configured to store instructions. A processor is configured by the instructions to control a catheter robot to manipulate an intracardiac echocardiography catheter swap views of the intracardiac echocardiography catheter intra-operatively based on pre-operatively selection of the views.

In a third aspect, a control system is provided for a steerable catheter. A robotic system is provided for operation of a steerable catheter. A memory is configured to store a first view of a heart and a second view of the heart. The first view is a different location and/or orientation than the first view from within the heart. The first and second views are views of anatomy and/or devices for a medical procedure. A processor is configured to cause the robotic system to navigate the steerable catheter from the first view to the second view in response to activation by a user. A display is configured to display an image of the first view and an image of the second view.

Other implementations of any of aspects 1-3 are summarized below as examples.

The present invention is defined by the following claims, and nothing in this section should be taken as a limitation on those claims. Features of one aspect or type of claim (e.g., method or system) may be used in other aspects or types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A workflow is provided for robotic intra-cardiac echocardiography guided transseptal puncture or another procedure. ICE imaging of the transseptal puncture workflow for catheter-based left heart procedures is, at least in part, automated. ICE catheter views (e.g., location and orientation) are pre-operatively specified from diagnostic imaging. The ICE catheter position within the patient anatomy is then intra-operatively localized. Catheter movement to the pre-specified target views is intra-operatively automated. Further, the physician-user can then iterate between target ICE catheter views hands-free as desired.

A software framework relies on a robotic system to manipulate the ICE catheter. Robotic controller software automatically steers the ICE catheter to a target. Automated view selection (e.g., pre-operatively) and swapping (e.g., intra-operatively) of views creates a clinical workflow mechanism for ICE-guided zero fluoroscopy in transseptal puncture. Fluoroscopic dose to physician and patient may be reduced by providing a consistent process for reduced or zero-fluoroscopy transseptal puncture. Better anatomical information for intra-procedural guidance may be provided by enabling a simple, automated ICE imaging workflow.

The pre-determination of desired views and automated swapping of views for imaging catheters may be used in other ICE-guided procedures. By selecting a different set of critical views preoperatively, the catheter robot may navigate to or between the views in any ICE procedure. As a specific example, by preselecting views of critical nearby anatomies to a procedure such as a transcatheter valve replacement, this framework can be applied for hands-free real-time complication monitoring during the procedure. Common complications in transcatheter valve replacements include valve annulus rupture, perforation of the myocardium, coronary ostia occlusion, aortic perforation or dissection, poor valve positioning, valve dislodgement, paravalvular leak, thrombus formation, and paracardial effusion. Views at different anatomy to monitor for any of these are set, and then swapped during the procedure by the catheter robot. In this or other procedures, one or more views of a device may be provided.

Figure 1:
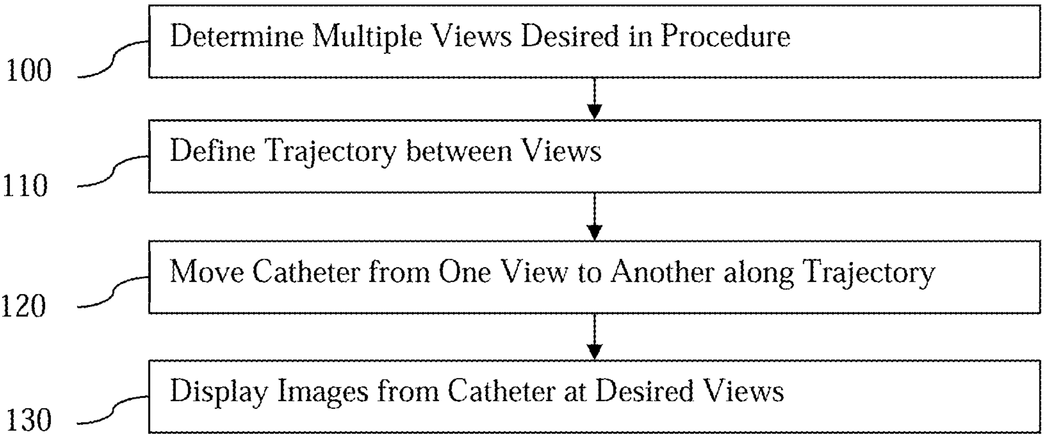
FIG. 1 is a flow chart diagram of one implementation of a method for robotically operating a catheter with swapping views.

FIG. 1 is a flow chart diagram of one embodiment of a method for robotic control of an imaging catheter, such as an ICE catheter. Different views are identified for the procedure. The catheter robot navigates the catheter to the location and orientation of the views with little or no need for user control, allowing the surgeon to focus on the procedure and control of other devices. By swapping between views automatically or semi-automatically, the imaging catheter provides monitoring, reducing the need for fluoroscopy while incurring little navigation burden to the operator.

Figure 2:
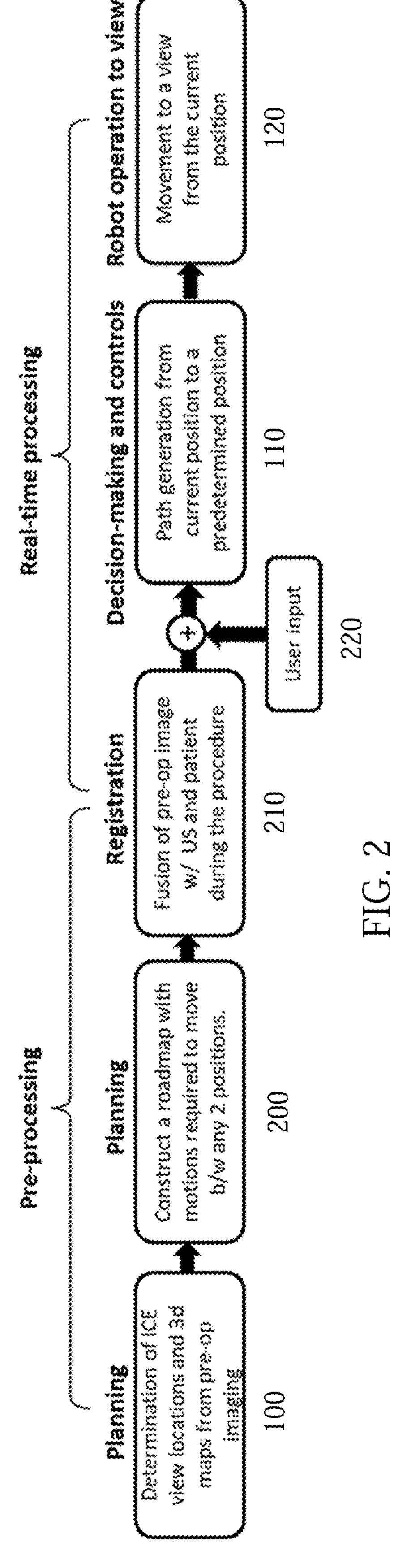
FIG. 2 is a flow chart diagram of another implementation of the method for robotically operating a catheter with swapping views.

FIG. 2 shows one implementation of the method of FIG. 1. FIG. 2 is a flow chart diagram of another approach for the method for robotic control of an imaging catheter.

Figure 5:
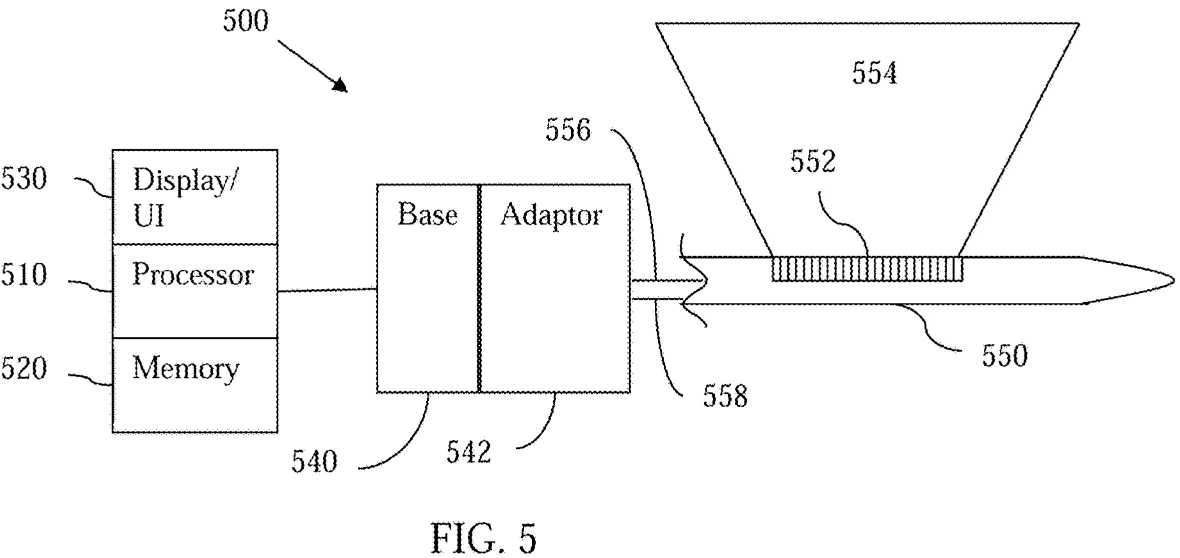
FIG. 5 is a block diagram of one embodiment of a system for view control of a robotic catheter system.

The method of FIGS. 1 and/or 2 is implemented by the system and/or robotic system of FIG. 5 or another system. A processor receives and/or a memory stores different views (e.g., locations and orientations of the transducer). The processor defines the trajectory and causes the catheter robot to move the catheter from one view to another view along the trajectory. The imaging catheter and imaging system (e.g., ultrasound system) generate images that are displayed on a display screen to monitor the patient, device, and/or procedure from the different views.

Additional, different, or fewer acts may be provided. For example, act 110 is not provided where the trajectory is pre-established or known. As another example, act 130 is not provided, such as where recordings of images are stored rather than displayed. In yet another example, acts 200, 210, and/or 220 are not provided in the method of FIG. 2 or are provided in the method of FIG. 1. In other examples, acts for pre-operative planning and/or pre, during, and/or post procedure imaging are provided. As another example, acts for puncture, ablation, stent placement, or another procedure operation on the heart are provided.

The acts are performed in the order shown (top to bottom or numerical) or a different order. For example, act 220 occurs prior to act 210 and/or after act 110.

In act 100, the processor determines a plurality of views by the imaging catheter in a heart for a procedure, such as transseptal puncture. The views are determined by input with a user interface, by an artificial intelligence, from an atlas, from procedure guidance, and/or loaded from memory.

The views may be standard views and/or views desired by a specific surgeon. The views may be with respect to a heart model or with respect to the heart of a specific patient. For example, ICE is used to view one or more locations of puncture, such as a primary and any secondary choices for heart wall puncture locations. One or more views are provided for each puncture location of the anatomy, such as from different angles, orientations, and/or distances. In another example, ICE is additionally, or alternatively, used to view the needle or other device used in the procedure. One or more views are provided for each desired position of the device, such as viewing a needle from different directions when placed adjacent to a puncture location. Any number of views of any object at any part of the procedure may be provided. These views are determined for monitoring the procedure with ICE.

The determination occurs in pre-operative planning. A three-dimensional (3D) map of the patient's heart may be used to define locations and orientations of an ultrasound transducer of the imaging catheter. The 3D map may form boundaries in which the view must be located and/or is used to determine where the view is desired. The views are defined relative to the heart in a pre-operative image. Alternatively, one or more views may be added or determined during the procedure and/or intra-operatively.

In one approach, ICE view locations are determined from preoperative imaging. Precise therapy planning on a computed tomography (CT) or magnetic resonance (MR) scan (image) is typical for electrophysiology and structural heart procedures. During this preoperative planning, the optimal ICE views to use during the transseptal puncture procedure are identified. The user precisely plans the positioning of the ICE catheter and the associated anatomic views. This determination of views may be performed manually. The user inputs the views directly within the CT imaging or heart segmentation from the imaging. This determination of views may be performed using an ICE simulator simulating the ICE within the pre-operative image. In either the manual entry or entry by simulation, the user specifies the ICE catheter location and image orientation (view) for different parts of the procedure. A predicted ICE view synthesized from the CT/MR data may be used to confirm that the desired views are selected. In another approach, the determination of one or more views is performed automatically, such as by an artificial intelligence trained for view determination for the procedure. In yet another approach, the determination is performed semi-automatically, such as a set of views output by a trained artificial intelligence with manual change and/or selection to adjust or define the views to be used. Simulation may be used to assist in selection or change.

In act 110, the processor defines a trajectory of movement of the imaging catheter between the views. A sequence of views and corresponding movements of the imaging catheter from view to view is defined. The trajectory is defined by path optimization by a processor and/or user selection or input. For example, simulation is used to define the path, where the trajectory is the path followed by the user in the simulation to get from one view to another. As another example, the processor uses boundaries from the 3D map or segmentation of the heart and any other blockage or no-go locations (e.g., where the needle is located) to find a shortest path between views.

The trajectory may be along a sequence of views. The imaging catheter will proceed from view to view along the trajectory. Alternatively, different trajectories are provided between different, any, or all pairs of views. The imaging catheter will move from any one view to a different selected view. Different views and corresponding trajectories may be used during the operation. In another approach, different trajectories are provided for different pairs or groups of views.

The trajectory is a path of movement along the degrees of freedom of the catheter. For example, four degrees of freedom are provided: translation along a longitudinal axis of the catheter, rotation about the longitudinal axis, anterior-posterior bend, and left-right bend. In other examples, six degrees of freedom in a patient-centric space is provided. The trajectory path is continuous or a series of two or more samples or points. The trajectory has a start and end, with no, one, two, or more waypoints or samples in between. The trajectory may be defined with respect to any movement within the degrees of freedom, such as rotation, translation, bend in one plane, bend in another plane, or combinations thereof. For example, the trajectory has translation along a curve in three dimensions with rotation and/or bending being different or the same at different points or samples along the path or curve. A straight trajectory or a trajectory with no translation (e.g., rotation and/or bending only) may be provided.

The path generation from a current position (e.g., view or manually located position) to a pre-determined or desired view of act 110 occurs pre-operatively, during the procedure (e.g., real-time processing and/or intra-operatively), or a combination of both. For example, the processor defines the trajectory during the operation based on the current location, the desired view (e.g., pre-determined view), and the 3D map. As another example, the trajectory is defined pre-operatively, such as using manual, automation (e.g., artificial intelligence), and/or semi-automatic entry in planning with the view determination.

FIG. 2 shows another approach. During the procedure, the planned views are loaded into the robotic controller, which can self-localize and automatically drive the ICE catheter to each of these views intra-operatively. Prior to the procedure, acts 200 and 210 are performed.

Figure 3:
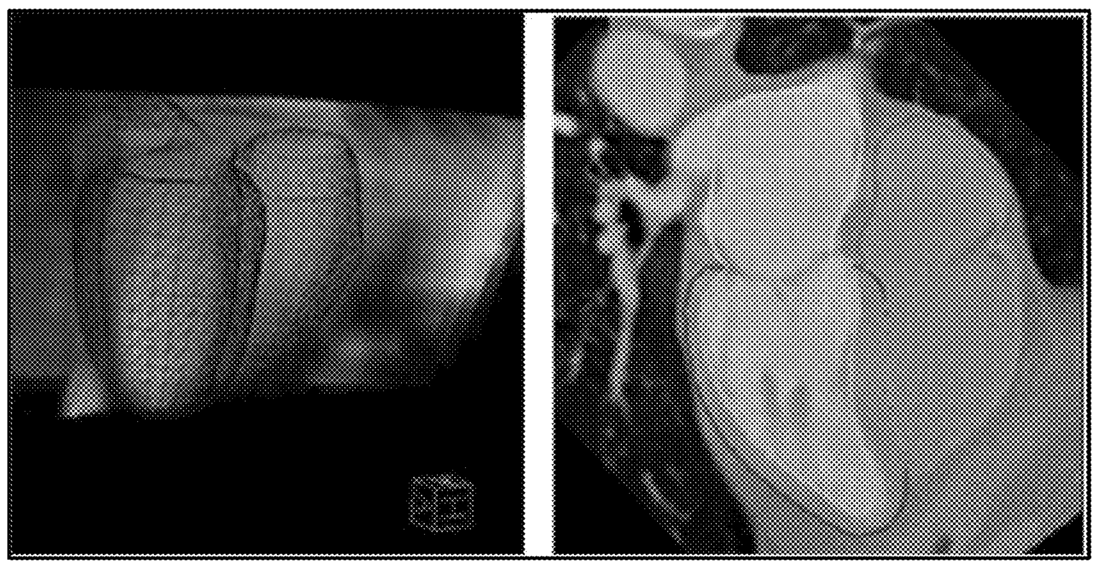
FIG. 3 illustrates example segmentations and corresponding boundaries for navigation and/or view placement.

A physical 3D boundary of the heart chamber is obtained. FIG. 3 shows one example where a mesh defines the heart boundary in 3D as well as a two-dimensional (2D) cross section of a heart with chamber boundaries. The boundary defines the overall possible workspace of ICE catheter manipulation (i.e., provides safe usage boundaries for robotic motion).

Figure 4:
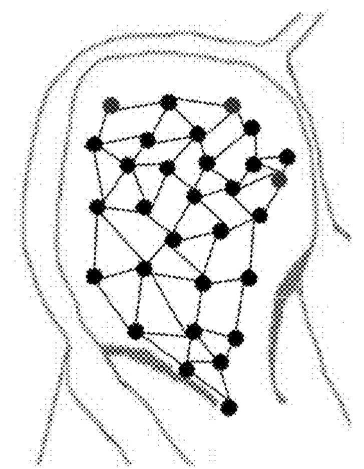
FIG. 4 two-dimensionally illustrates view positions and trajectory formation according to one example.
Figure 4:
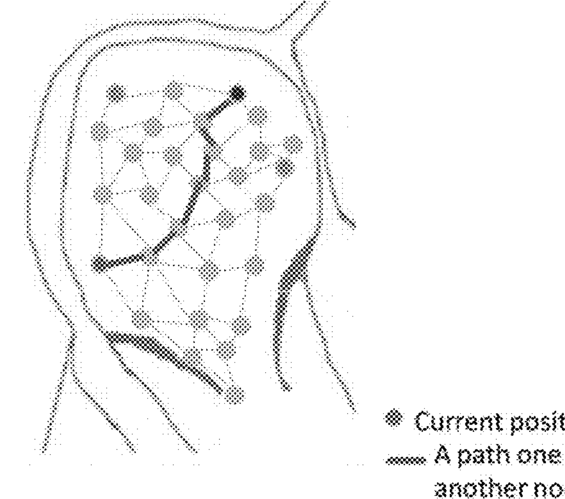

In act 200, the processor constructs a roadmap with motions to move between various positions within the boundaries. The left side of FIG. 4 shows an example roadmap as a plurality of positions (dots) and links between the positions. The links are the routes or trajectories between adjacent positions within the boundary.

Paths within the heart volume are generated. The optimal robotic control inputs that can manipulate the catheter from some current position within the heart to a desired predetermined view may be derived from this roadmap of paths. The desired ICE view pose information as well as 3D heart chamber safe-passage volume (i.e., occlusion map) are used to form the roadmap, such as including the views within the boundaries as part of the roadmap. A discrete grid within the occlusion map is generated where some locations include locations of the desired views. Other locations are between the desired views, such as along a grid. Robot kinematics modeling determines a set of robotic controls to move between any two points in the grid, such as between desired views. A kinematics model for catheter manipulation is used as a set of possible motions in the preprocessing step. The catheter state $X=(x, y, z, x\theta, y\theta, z\theta)$ where $\in\chi$ has $(x,y,z)$ as the position of the end-tip of the catheter/guidewire in $R^3$ (robotic system coordinate) and $\theta$ (robotic system rotation) as the orientation, respectively. The manipulation system can be treated as a transition function F. Using control $u \in U$,F makes the transition from $X(k)$ to another state $X(k+1)$:$X(k+1)=X(k)+\omega, \omega \sim N(Xp, \Sigma p)$, where $X_p$ and $\Sigma p$ are the mean and variance of the catheter state transitions via u. The transition error is minimized with hysteresis compensation. The result is the 3D occlusion map and motion models.

The roadmap is constructed from the 3D occlusion map (boundary) and motion models. The Probabilistic Roadmap (PRM) builds a single roadmap that aims to cover a good portion of the collision-free space area in the 3D occlusion map as shown FIG. 4, left side, in two dimensions. A probabilistic roadmap covers the maximal space within the boundary. Other approaches, such as forming trajectories without the roadmap, may be used.

In act 210 of FIG. 2, the processor registers the pre-operative planning (e.g., boundary, views, trajectories, and/or roadmap) with the patient. The registration occurs during the procedure, such as after positioning of the patient and prior to surgery.

Landmarks, fiducials, imaging of the catheter within the patient, position sensing, or other approaches may be used to register the desired views to the heart of the patient. In one approach, preoperative image data and the plan are fused with patient imaging during the procedure. This co-registration procedure can be done using CT-to-x-ray registration (2D/3D), CT-to-DynaCT (3D/3D), or CT-to-ultrasound if a sufficiently large ICE 3D volume is available. Several methods can be utilized for the co-registration (including rigid and deformable) based on image-based registration or deep learning algorithms.

If accomplished by CT-to-x-ray or CT-to-DynaCT, the robotic ICE controller is then registered to the scene or patient. For example, the user positions the ICE catheter at a series of standard anatomical views that have previously been identified within the CT data, such as the desired views for the procedure or other views. Alternatively, two x-ray images can be acquired to estimate the pose of the ICE catheter. As another approach, sensors directly embedded within the ICE catheter are used to register.

If registration is accomplished by CT-to-ultrasound, no additional co-registration step is required. It may be useful to co-register the x-ray or DynaCT into the scene. CT-to-x-ray and CT-to-DynaCT fusion are beneficial, but not necessary. CT-to-ultrasound fusion aligns the preoperative plan to the patient during treatment.

In the approach of FIG. 2, the selection or generation of the trajectory or trajectories of act 110 is performed during the operation in real time using the registered roadmap. The processor selects the trajectory from the roadmap of motions confined to a boundary of the heart.

For example, one or more paths from a current position to a predetermined position are selected. Given a road map, the optimal path from one pose to another (e.g., between predetermined views) is found. The catheter is to be manipulated from the current pose to the target pose, making all state transitions via the robot actuators, finding an optimal sequence of motions $\pi'$ that minimizes $\zeta(\pi)$, which is described as $\pi^*=\text{argmin}\ \zeta(\pi)$. A discrete search (e.g., A*) algorithm finds the optimal sequential path from one location to another location. FIG. 4, right side, shows selection of a path in the road map. The path is shown as a bold line from a current position to another position, such as a desired view. The kinematics and planning for the robotic ICE controller can be applied either by traditional optimization approaches or by deep learning algorithms.

In act 120, the processor moves the imaging catheter. The control processor causes the robotic catheter system to move the imaging catheter. The processor controls the robotic catheter system to move the catheter. For example, the processor causes the robotic catheter system to translate, rotate, and/or bend the catheter while part of the catheter is in the patient.

The movement is along the trajectory. The trajectory defines the translation, rotation, and/or bending. The processor causes the robotic catheter system to translate, rotate, and/or bend the catheter to move the catheter along the trajectory. The movement is from a current position, such as one desired view, to another desired view. The movement swaps between views. The trajectory is followed to change between desired views of the procedure.

The movement of the imaging catheter occurs intra-operatively or during the procedure. The pre-operative determination of the desired views is used to move the imaging catheter during the operation to show or image at the different views at different times for monitoring.

The movement is automatic or semi-automatic. The user can either set the robotic catheter system to automatically move (e.g., continuously swap or hop) between desired views or have more in-depth control by semi-automatic moving view-by-view (e.g., one button press or activation at a time causes the robotic catheter system to move the catheter to the next desired or a specific desired view). In act 220, the processor receives user input to swap views. The trajectory to the desired view for the swap of views is defined or looked-up and used to move the imaging catheter to provide the next desired view in response to the user input. After each activation, the robotic catheter system pauses the movement at the desired view. Automatic navigation occurs in response to user activation input and without user control of the moving along the trajectory. Hands-free movement of the imaging catheter is provided. Some user control, such as override, of the movement may be provided.

The user input may be an indication of activation or may be selection of a desired view. For example, the movement is in response to input by the user of a selection of one of the determined views. For the FIG. 2 example, the robotic control, pathing, and view locations are determined preoperatively. The user only inputs identification of which view is desired at that time. For other method examples, the view order is pre-determined so activation cycles to a next view. The pathing and movement occur during the procedure to swap views. Alternatively, the pathing occurs prior to the operation.

The user input is provided through a graphical user interface, voice command, foot pedal, table-mounted button, gesture, controller, or another input. The desired view may be selected from a list, selected from the road map, indicated on a 3D rendering, or provided as a next view in a list. For example, the user presses a button to cause movement to a next view of the determined views without indication of a specific view at the time of user input during the operation.

The movement of act 120 is performed by the catheter robot after decision-making and control for the next view. Movement is to a view from the current position, such as swapping between different ones of the pre-determined views. The catheter robot precisely manipulates each of the 4 DOF of the ICE catheter, and, by extension, the tip of the catheter or the imaging transducer. A motor control sequence is applied by the robotic controller. Since the catheter robot is co-registered to the patient, the control sequence moves the ICE catheter from the current position to the desired position and orientation (i.e., the desired view).

In one implementation, the processor causes the robotic catheter system to repeat movement of the imaging catheter from desired view to desired view multiple times. Back and forth swapping occurs for regular or continuous monitoring using the imaging catheter. The navigation of the imaging catheter is performed without the operator performing the navigation. The user may start or activate the swap, but the robotic catheter system navigates the catheter along the trajectory with or without pauses at waypoints without further input or control by the user.

Physicians typically survey anatomy with ICE to view how devices interact or have deployed over a region. By swapping between the determined views, hands-free repeat image surveying of anatomy and device deployment is provided. The user is free to focus more on the images and control of other devices.

In another approach, the processor causes the robotic catheter system to move the catheter in synchronization with heart motion. Using ECG or image processing, the heart cycle or trace is input to the processor or a trigger device. The robotic catheter system moves the catheter during a particular point or part of the heart cycle.

For moving, the processor controls the motors of the robotic catheter system. The robotic catheter system, by actuation of the motors, manipulates the catheter. The manipulation may include steering (e.g., bending in one or more planes), global rotation (e.g., rotation of the handle and corresponding catheter), global translation (e.g., pulling or pushing the catheter further out or further into the patient), imaging, ablation, puncture, inflation, stitching, clamping, cutting, pharmaceutical deposit, stent expansion, balloon inflation, stent release, and/or another operation. The robot, under control of the processor, operates the catheter. Similarly, the user interface (e.g., display and input devices) of the robotic catheter system provides manual control of the robotic catheter system. The processor may receive the inputs and/or generate the outputs for the user interface and provide controls to the motors.

In act 130, a display displays one or more images from the imaging catheter. For ICE, the images are ultrasound. For an endoscope or catheter with an optical camera, the images are optical. The images are of the desired views, such as of anatomy and/or devices (e.g., needles) of interest in the procedure. A single image or a sequence of images from one view may be provided. Images while the imaging catheter moves may also be displayed.

Due to the swapping during the procedure, images from different views are displayed sequentially. The surgeon may monitor the procedure as needed by imaging from the different views.

FIG. 5 is a block diagram of one embodiment of a catheter control system. A control system using a robotic catheter system (catheter robot) 500 is provided for a steerable catheter 550. The control system uses different views for swapping between views from the catheter 550, freeing the user to concentrate on imaging information and/or other operations than navigating the catheter 550.

The control system includes the robotic catheter system 500 formed by the base 540 and adaptor 542. The processor 510, memory 520, and/or display 530 are part of a separate computer, workstation, or server and/or are part of the robotic catheter system 500. Additional, different, or fewer components may be provided. For example, the base 540 and adaptor 542 are combined to be one housing for motors and clamps to manipulate the catheter 550.

The robotic catheter system 500 is configured for robotically controlling the catheters 450. In an example used herein, the robotic catheter system 500 is configured to control an ICE catheter 550. Other types of steerable catheters may be used, such as controlling an ablation catheter or another imaging catheter. Other catheter-like devices (e.g., fiber optic endoscope or needle) may be controlled. These different catheters may have the same or different arrangements of control knobs, steering, degrees of freedom, and/or operation, so the robotic catheter system 500 is configured to operate or control the arrangements of the catheter 550 being used.

Any type or design of robotic catheter system 500 may be used. In the example herein, the robotic catheter system 500 includes the base 540 and an adaptor 542. The base 540 includes the motors for steering and/or operating the catheter 550, and the adaptor 542 is configured to mate with, hold, and/or manipulate the catheter 550. For example, the adaptor 542 allows the robotic catheter system 500 to operate the steerable ICE catheter 550 designed for manual control by a physician. U.S. Pat. No. 11,590,319, the disclosure of which is incorporated herein by reference, discloses various embodiments of such a robotic catheter system. Other designs may be used, such as robotic catheter systems designed to robotically control a catheter designed specifically for or to mate with and be controlled by the robot (e.g., no adaptor 542).

The base 540 includes motors to manipulate the steerable catheter 550 in any number of degrees of freedom, such as 4 or more degrees of freedom (e.g., global translation, global rotation, and bending or steering the catheter 550 in two or more directions or planes). Gearing, motors, grippers (clamps), connectors, and/or other robotic components are in the base 540 for generating and transmitting force to operate the catheter 550. The robotic catheter system 500 applies push and/or pull forces to steering wires 556, 558 (e.g., three or four steering wires per catheter 550) to operate the catheter 550. The tip is steered for catheter operation. Electrical signals, translation, and/or rotation force may be generated in the base 540. Global translation and/or rotation forces may similarly be applied, such as through the handle of the catheter 550.

The adaptor 542 connects or plugs to the base 540 and manipulates the catheter 550. In one embodiment, the adaptor 542 is a clamshell or other arrangement of housing, gearing, connectors, clamps, and/or other robotic components to transfer force from the base 540 to the catheter 550 to steer and/or otherwise operate the catheter 550. In one approach, the adaptor 542 fits around the handle and/or body of the catheter 550 to allow for manipulating the actuators (e.g., knobs) of the catheter 550, for instance AP/LR knobs of an ICE catheter and/or the handle of the catheter 550 for global translation and/or rotation (e.g., push-pull knob of an ablation catheter, etc.). Other adaptors 542 that support other degrees of freedom (e.g., 2, 3, 4, or more) may be used, such as for control of needle or ablation catheters.

Where the steerable catheter 550 is an ICE catheter, the robotic catheter system 500 may be configured to control the ICE catheter. The robotic catheter system 500 or an imaging system may control the imaging using the imaging catheter. The array 552 of elements is controlled through beamforming to generate ultrasound images. The field of view 554, type of imaging, and/or other imaging control may be provided.

The memory 520 is a non-transitory memory, such as a removable storage medium, a random-access memory, a read only memory, a memory of a field programmable gate array, a cache, and/or another memory. The memory 520 is configured by a processor, such as the processor 510, to store views (position and orientation), road map (movement options), motion controls, trajectories, images, waypoints, control signals, boundaries, registration, information, control software, instructions executable by the processor 510, instructions executable by the robotic catheter system 500, interface software, and/or other information.

In one implementation, the memory 520 stores the determined views registered to the heart of the patient. For example, the memory 520 is configured to store two or more views of a heart with coordinate systems transformed or transformable to the robotic catheter system 500 and/or the patient. One view is at a different location and/or orientation than another view from within the heart. The different views are views of anatomy and/or devices for a medical procedure. The different views are stored in the memory as selections from a pre-operative image of the heart or other source.

The processor 510 is a general processor, application specific integrated circuit, integrated circuit, digital signal processor, field programmable gate array, artificial intelligence processor, tensor processor, and/or another controller for interfacing with or controlling the robotic catheter system 500, the user interface/display 530, and/or catheter 550. The processor 510 is configured by design, hardware, firmware, and/or software to interface between the user and robotic catheter system 500 and/or to control the robotic catheter system 500. Multiple processors may be used for sequential and/or parallel processing as the processor 510. The instructions from the memory 520, when executed by the processor 510, cause the processor 510 to operate the robotic catheter system 500 and/or the steerable catheter 550 and to interface between various components and/or with the user or operator.

The processor 510 is in a same room as the robotic catheter system 500. For example, a computer or workstation is connected with wires or wirelessly for interacting with the robotic catheter system 500. In one implementation, the processor 510 is a processor of the robotic catheter system 500. Alternatively, the processor 510 is in a different room than the robotic catheter system 500, such as in a room of the same building, different building, different facility, or different region. Computer network communications are used between the processor 510 and the robotic catheter system 500. The control through the processor 510 for the robotic catheter system 500 allows the processor 510 to be fully remote from the procedure, patient, and/or robotic catheter system 500 as the processor 510 provides for the catheter 550 to be manipulated robotically.

The desired views are stored in the memory 520. As the operator controls the robotic system 500 to move the catheter 550 and/or the user interface 530 to enter selection of a desired view, the trajectory is created and stored in the memory 520 or selected from the memory 520. The processor 510 is configured to cause the robotic system 500 to navigate the steerable catheter 550 using the trajectory so that the desired view is provided. The processor 510 is configured by the instructions to control the catheter robot 500 to manipulate the ICE catheter to swap views of the ICE catheter intra-operatively based on pre-operatively selection of the views.

The processor 510 is configured to receive the selection of the views in pre-operative images. Each selected view defines a location and orientation. The views are stored in the memory 520. A different processor may be used to receive the selected views.

The processor 510 is configured to manipulate the ICE catheter hands-free by a user in response to activation of the swap by the user. Using the selected views, the processor 510 causes the catheter robot 500 to navigate the ICE catheter to the desired view. The navigation occurs in response to input from the user, such as activation or view selection. The navigation itself to move from the current position to the selected position is hands-free by the user or requires less than full navigation control by the user (e.g., handles one or more degrees of freedom automatically).

The processor 510 is configured to perform the swap from one view to another view. The ICE catheter follows a pre-planned or real-time optimized trajectory between views. For example, the trajectory to implement the swap is based on optimization of a path length from one view to another view. The processor 510 causes the swap from one view to another view during the procedure, such as for a transseptal puncture. Imaging from the imaging catheter 550 is provided for different views to monitor transseptal puncture or other heart procedure. The swap occurs in response to activation by the user but may instead be triggered by a procedure event and/or be periodic.

The display/user interface 530 is a display screen, such as a liquid crystal display or monitor, and a user input, such as a keyboard, knobs, sliders, touchpad, mouse, and/or trackpad. The display/user interface 530 may include icons, graphics, or other imaging, such as from an operating system or application, for user interaction (selection, activation, and/or output).

The display 530 is configured to display images from the imaging catheter 550, such as ultrasound images. The images are of the desired views. Since the views are swapped during the procedure, the images of the views are provided in sequence. Images from different perspectives (locations and/or orientations) assist in monitoring the procedure.

Various examples and corresponding combinations are provided below.

In example 1, a method for robotic control of an imaging catheter is provided. A plurality of views by the imaging catheter in a heart for transseptal puncture are determined. A trajectory of movement of the imaging catheter between the views of the plurality is defined. A robotic catheter system moves the imaging catheter between the views of the plurality along the trajectory. Images from the imaging catheter at the views of the plurality are displayed.

Example 2 is the method of example 1 wherein moving and displaying are performed intra-operatively based on pre-operative performance of determining.

Example 3 is the method of examples 1 or 2 wherein moving comprises automatic navigation in response to user activation input and without user control of the moving along the trajectory.

Example 4 is the method of any of examples 1-3 wherein determining comprises determining the views of the plurality as one or more views of one or more locations for the transseptal puncture and/or one or more views of a needle for performing the transseptal puncture.

Example 5 is the method of any of examples 1-4 wherein determining comprises defining locations and orientations of an ultrasound transducer of the imaging catheter in a pre-operative image.

Example 6 is the method of any of examples 1-5 wherein defining comprises selecting the trajectory from a roadmap of motions confined to a boundary of the heart.

Example 7 is the method of any of examples 1-6 wherein moving comprises moving from a first of the views to a second of the views.

Example 8 is the method of any of examples 1-7 wherein moving comprises moving in response to input of a user selection of one of the views.

Example 9 is the method of any of examples 1-8 wherein moving comprises hand-free moving of the imaging catheter.

Example 10 is the method of any of examples 1-9 wherein moving comprises swapping between different ones of the views.

Example 11 is a catheter control system comprising: a memory configured to store instructions; and a processor configured by the instructions to control a catheter robot to manipulate an intracardiac echocardiography catheter swap views of the intracardiac echocardiography catheter intra-operatively based on pre-operatively selection of the views.

Example 12 is the catheter control system of example 11 further comprising the catheter robot.

Example 13 is the catheter control system of any of examples 11-12 wherein the processor is configured to manipulate the intracardiac echocardiography catheter hands-free by a user in response to activation of the swap by the user.

Example 14 is the catheter control system of any of examples 11-13 wherein the processor is configured to receive the selection of the views in pre-operative images, the selection defining a location and orientation for each of the views.

Example 15 is the catheter control system of any of examples 11-14 wherein the processor is configured to perform the swap from a first of the views to a second of the views with the intracardiac echocardiography catheter following a trajectory based on optimization of a path length from the first view to the second view.

Example 16 is the catheter control system of any of examples 11-15 wherein the processor is configured to perform the swap from a first of the views for a transseptal puncture to a second of the views for the transseptal puncture.

Example 17 is the catheter control system of any of examples 11-16 further comprising a display configured to display ultrasound images of the views in sequence from the swap.

Example 18 is a control system for a steerable catheter. The control system comprising: a robotic system for operation of a steerable catheter; a memory configured to store a first view of a heart and a second view of the heart, the first view being a different location and/or orientation than the first view from within the heart, the first and second views being views of anatomy and/or devices for a medical procedure; a processor configured to cause the robotic system to navigate the steerable catheter from the first view to the second view in response to activation by a user; and a display configured to display an image of the first view and an image of the second view.

Example 19 is the control system of example 18 wherein the processor is configured to cause the navigation in response to input from the user, the navigation being hand-free by the user.

Example 20 is the control system of examples 18 or 19 wherein the first view and the second view are stored in the memory as selections from a pre-operative image of the heart.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for robotic control of an imaging catheter, the method comprising:

determining a plurality of views by the imaging catheter in a heart for transseptal puncture, the determining being selection of the views of the plurality in a pre-operative image, wherein each view of the plurality of views defines a respective location and orientation of an ultrasound transducer of the imaging catheter;

defining a trajectory of movement of the imaging catheter between the views of the plurality;

registering the pre-operative image and the views of the plurality with a patient;

moving, by a robotic catheter system, the imaging catheter between the views of the plurality of views along the trajectory in the patient based on the registration, wherein moving the imaging catheter comprises automatically navigating the imaging catheter from a first view of the plurality of views to a second view of the plurality of views to swap views in response to a user activation input, without user control of the imaging catheter along the trajectory; and displaying images from the imaging catheter at the views of the plurality.

2. The method of claim 1 wherein moving and displaying are performed intra-operatively based on pre-operative performance of determining.

3. The method of claim 1 wherein determining comprises determining the views of the plurality as one or more views of one or more locations for the transseptal puncture and/or one or more views of a needle for performing the transseptal puncture.

4. The method of claim 1 wherein defining comprises selecting the trajectory from a roadmap of motions confined to a boundary of the heart.

5. The method of claim 1 wherein moving comprises moving in response to input of a user selection of one of the views.

6. The method of claim 1 wherein moving comprises hand-free moving of the imaging catheter.

7. A catheter control system comprising:

a memory configured to store instructions; and a processor configured by the instructions to control a catheter robot to physically manipulate an intracardiac echocardiography catheter to swap real-time imaging views captured by the intracardiac echocardiography catheter intra-operatively based on pre-operative selection of the views.

8. The catheter control system of claim 7 further comprising the catheter robot.

9. The catheter control system of claim 7 wherein the processor is configured to manipulate the intracardiac echocardiography catheter hands-free by a user in response to activation of the swap by the user.

10. The catheter control system of claim 7 wherein the processor is configured to receive the selection of the views in pre-operative images, the selection defining a location and orientation for each of the views.

11. The catheter control system of claim 7 wherein the processor is configured to perform the swap from a first of the views to a second of the views with the intracardiac echocardiography catheter following a trajectory based on optimization of a path length from the first view to the second view.

12. The catheter control system of claim 7 wherein the processor is configured to perform the swap from a first of the views for a transseptal puncture to a second of the views for the transseptal puncture.

13. The catheter control system of claim 7 further comprising a display configured to display ultrasound images of the views in sequence from the swap.

14. A control system for a steerable catheter, the control system comprising:

a robotic system for operation of a steerable catheter;

a memory configured to store a first view of a heart and a second view of the heart, the first view being a different location and/or orientation than the second first view from within the heart, the first and second views being views of anatomy and/or devices for a medical procedure, the first and second views being defined in a pre-operative image, wherein the first view defines a first physical location and orientation of the steerable catheter and the second view defines a second physical location and orientation of the steerable catheter;

a processor configured to register the pre-operative image with a patient and to cause the robotic system to physically navigate the steerable catheter from the first physical location and orientation of the first view to the second physical location and orientation of the second view in response to activation by a user and based on the registration; and a display configured to display an image of the first view and an image of the second view.

15. The control system of claim 14 wherein the processor is configured to cause the navigation in response to input from the user, the navigation being hand-free by the user.

16. The control system of claim 14 wherein the first view and the second view are stored in the memory as selections from a pre-operative image of the heart.

* * * * *